United States Patent
Barak et al.

(10) Patent No.: US 10,564,106 B2
(45) Date of Patent: Feb. 18, 2020

(54) RAMAN SPECTROSCOPY BASED MEASUREMENTS IN PATTERNED STRUCTURES

(71) Applicant: NOVA MEASURING INSTRUMENTS LTD., Rehovot (IL)

(72) Inventors: Gilad Barak, Rehovot (IL); Yanir Hainick, Tel-Aviv (IL); Yonatan Oren, Kiryat Ono (IL); Vladimir Machavariani, Rishon Lezion (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

(21) Appl. No.: 16/062,114

(22) PCT Filed: Dec. 15, 2016

(86) PCT No.: PCT/IL2016/051349
§ 371 (c)(1),
(2) Date: Jun. 14, 2018

(87) PCT Pub. No.: WO2017/103934
PCT Pub. Date: Jun. 22, 2017

(65) Prior Publication Data
US 2018/0372644 A1 Dec. 27, 2018

Related U.S. Application Data

(60) Provisional application No. 62/267,291, filed on Dec. 15, 2015.

(51) Int. Cl.
*G01N 21/65* (2006.01)
*G01B 11/06* (2006.01)
(Continued)

(52) U.S. Cl.
CPC ......... *G01N 21/65* (2013.01); *G01B 11/0666* (2013.01); *G01L 1/24* (2013.01);
(Continued)

(58) Field of Classification Search
CPC .. G01N 21/65; G01N 21/658; G01N 21/9501; G01B 11/0666; G01B 2210/56; G01L 1/24; G03F 7/70625; H01L 22/12
See application file for complete search history.

(56) References Cited

U.S. PATENT DOCUMENTS 6,151,119 A * 11/2000 Campion ........... G01B 11/0666
356/630
7,274,440 B1  9/2007 Janik
(Continued)

*Primary Examiner* — Dominic J Bologna
(74) *Attorney, Agent, or Firm* — Alphapatent Associates, Ltd; Daniel J. Swirsky

(57) ABSTRACT

A method and system are presented for use in measuring one or more characteristics of patterned structures. The method comprises: providing measured data comprising data indicative of at least one Raman spectrum obtained from a patterned structure under measurements using at least one selected optical measurement scheme each with a predetermined configuration of at least one of illuminating and collected light conditions corresponding to the characteristic (s) to be measured; processing the measured data, and determining, for each of the at least one Raman spectrum, a distribution of Raman-contribution efficiency (RCE) within at least a part of the structure under measurements, being dependent on characteristics of the structure and the predetermined configuration of the at least one of illuminating and collected light conditions in the respective optical measurement scheme; analyzing the distribution of Raman-contribution efficiency and determining the characteristic(s) of the structure.

13 Claims, 4 Drawing Sheets

(51) Int. Cl.
*G01N 21/95* (2006.01)
*G03F 7/20* (2006.01)
*H01L 21/66* (2006.01)
*G01L 1/24* (2006.01)

(52) U.S. Cl.
CPC ....... *G01N 21/658* (2013.01); *G01N 21/9501* (2013.01); *G03F 7/70625* (2013.01); *H01L 22/12* (2013.01); *G01B 2210/56* (2013.01)

(56) References Cited

U.S. PATENT DOCUMENTS

| | | | |
|---|---|---|---|
| 7,433,056 B1 * | 10/2008 | Janik | G01B 11/0616 356/301 |
| 2008/0049300 A1 | 2/2008 | Kanner | |

* cited by examiner

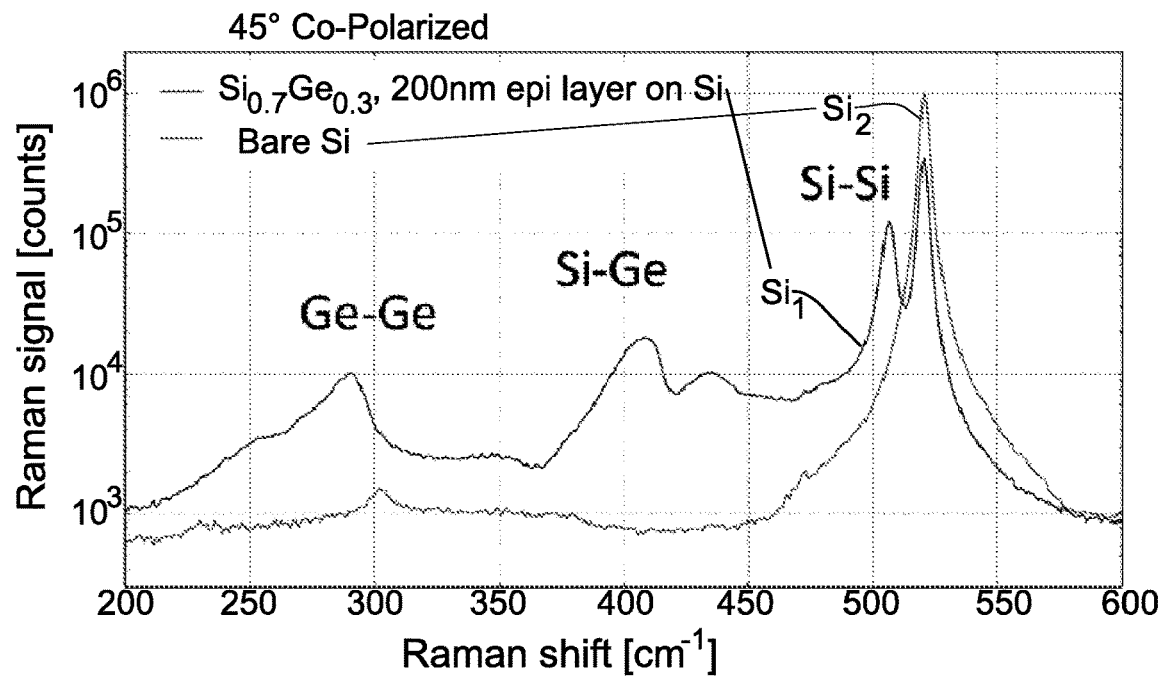
FIG. 1 (General Art)
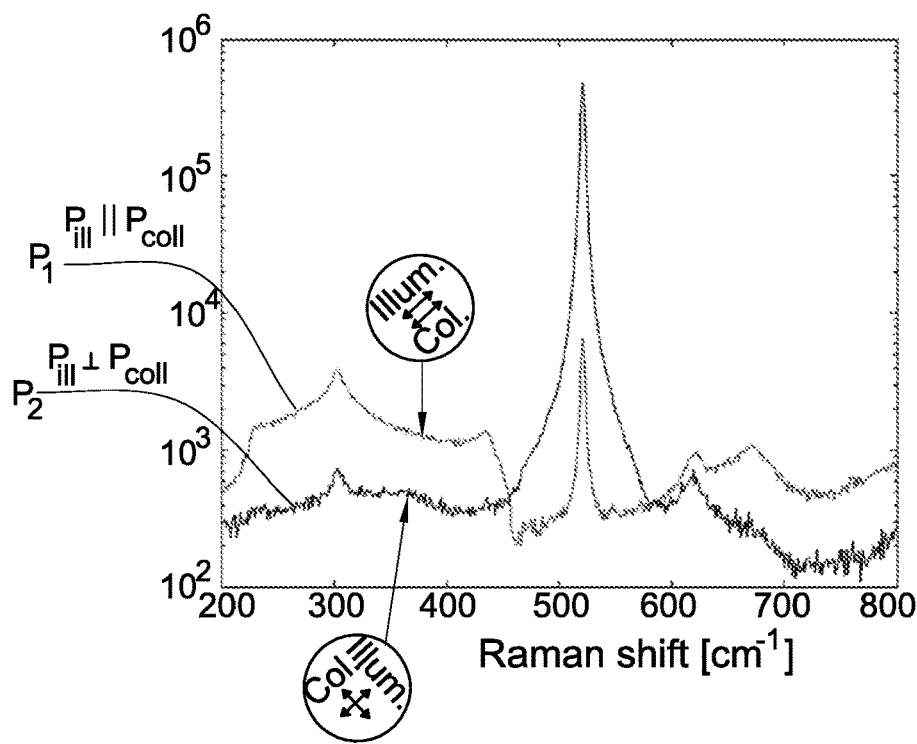
FIG. 2

Raman signal from Si grating in SiO₂, λ=405

Raman signal from Si grating in SiO₂, λ=532

RAMAN SPECTROSCOPY BASED MEASUREMENTS IN PATTERNED STRUCTURES

CROSS-REFERENCE TO RELATED APPLICATIONS

This application is a U.S. National Phase Application under 35 U.S.C. 371 of International Application No. PCT/IL2016/051349, which has an international filing date of Dec. 15, 2016, and which claims the benefit of priority from U.S. Provisional Patent Application No. 62/267,291, filed Dec. 15, 2015, the disclosure of which is incorporated herein by reference in its entirety.

TECHNOLOGICAL FIELD

The present invention is in the field of metrology techniques, and relates to a method and system for measuring various parameters/properties of patterned structures, such as semiconductor wafers, using Raman spectroscopy based measurements.

BACKGROUND

The growing complexity of semiconductor device designs in advanced technology nodes involves not only a decrease in structural dimensions and higher complexity of the device design, but also the utilization of new materials. Device yield and performance become increasingly sensitive to material properties, such as composition, stress, crystallinity and doping, which in turn require appropriate metrological solutions for process control.

Various optical measurement techniques have been developed for measuring the strain and other properties of a material.

U.S. Pat. No. 7,274,440 describes systems and methods for measuring stress in a specimen. One system includes an optical subsystem configured to measure stress-induced birefringence in patterned structures formed on the specimen. In some embodiments, the optical subsystem may be configured as a spectroscopic ellipsometer, a multi-angle laser ellipsometer, a polarimeter, a polarized reflectometer, or some combination thereof. The system also includes a processor coupled to the optical subsystem. The processor is configured to determine stress in a material of the patterned structures using the stress-induced birefringence measurements. One method includes measuring stress-induced birefringence in patterned structures formed on the specimen using an optical technique. The method also includes determining stress in a material of the patterned structures using the stress-induced birefringence measurements.

GENERAL DESCRIPTION

The present invention provides a novel approach for measuring various structure parameters, especially useful for controlling the process of structure manufacture. This is based on the inventors' understanding that, although some technologies, such as (X-ray Diffraction (XRD), High-Resolution X-ray Diffraction (HRXRD), X-ray Fluorescence (XRF), X-ray Photoelectron Spectroscopy (XPS), Low energy Electron induced X-ray Emission Spectrometry (LEXES), provide relevant information about the patent structure's parameters, there is a need for a good solution which adequately satisfies the stringent sensitivity and throughput requirements for controlling the manufacture of patterned structures, in particular semiconductor process control.

The present invention presents a novel methodology for advanced characterization of semiconductor structures' properties (generally, patterned structures). Example for such properties are material composition, stress and doping.

The invention is based on using Raman Spectroscopy at specific measurement configurations (e.g. polarization configurations), typically in conjunction with suitable modeling capabilities, in order to highlight and isolate sensitivity to the parameters of interest, as well as to distinguish between sensitivity to different material parameters.

Raman spectroscopy is an established technology, with extensive literature describing its usage for the characterization of various material properties. However, as described more specifically below, correct control over illumination and collection channels attributes, as well as the accompanying signal processing and modeling tools, are critical to enable accurate measurements using this method.

The Raman spectrum carries information on various properties of the probed sample. Most notably, different peaks in the spectrum correspond to different materials. When the measured target is comprised of material compounds (e.g. SiGe), specific peaks in the Raman spectrum would correspond to different atom pairs (e.g. Si—Si, Si—Ge and Ge—Ge).

In this connection, reference is made to FIG. 1 exemplifying the Raman spectrum from a thin SiGe layer deposited over Si (graph $S_1$), as well as pure (bulk) Si for reference (graph $S_2$). In the SiGe measurement, four peaks are clearly observed. The strong peak at 520 $cm^{-1}$ corresponds to Si—Si vibrations in the substrate. The three additional peaks correspond to Si—Si, Si—Ge and Ge—Ge pairs in the SiGe film. In the pure-Si reference spectrum, only the substrate Si—Si peak is observed. Thus, the presence of a SiGe layer gives rise to three additional peaks, associated with the vibrations of different atom pairs in the layer.

Methods for extracting information on concentration and stress from the positions of these peaks are well known in the literature. For example, a set of equations relating the positions of the three SiGe peaks with the Germanium composition and the layer stress, is presented in the following publication: T. S. Perov et al., *Composition and strain in thin $Si_1$-xGex virtual substrates measured by micro-Raman spectroscopy and x-ray diffraction*, J. App. Phys. 109, 033502 (2011).

Doping is another characteristic which affects the Raman spectrum. Carrier concentration, arising from the dopant distribution, affects the Raman signal and causes an additional \ shift in the Raman peaks. The level of doping can hence be incorporated into the fitting procedure, and concurrent assessment of doping level along with stress and composition is possible through monitoring peak locations (see for example—A. Perez-Rodriguez et al., *Effect of stress and composition on the Raman spectra of etch-stop SiGeB layers*, J. Appl. Phys. 80, 15 (1996).

The present invention provides a novel metrology method and device, configured to allow optimized Raman-metrology for the sample characteristics of interest. This approach allows access to multiple properties of the sample, and specifically applies also to metrology of nanostructured devices.

Also, the present invention provides a set of modeling solutions (methods and systems) to allow correct utilization of these methods and degrees of freedom in the device configuration, as well as accurate interpretation of the Raman measurements.

The above two aspects of the invention can be used separately, with substantial potential benefit to either. Conversely, used together they can lead to significantly improved metrological performance, as will be discussed below.

Thus, according to one broad aspect of the invention, it provides a method for use in measuring one or more characteristics of patterned structures. The method comprises:

providing measured data comprising data indicative of at least one Raman spectrum obtained from a patterned structure under measurements using at least one selected optical measurement scheme each with a predetermined configuration of at least one of illuminating and collected light conditions corresponding to said one or more characteristics to be measured;

processing the measured data, and determining, for each of said at least one Raman spectrum, a distribution of Raman-contribution efficiency across at least a part of the structure under measurements, being dependent on characteristics of the structure and said predetermined configuration of the at least one of illuminating and collected light conditions in the respective optical measurement scheme;

analyzing said distribution of Raman-contribution efficiency and determining said one or more characteristics of the structure.

The one or more characteristics of the structure to be measured comprises at least one of the following: dimension, material composition, stress, crystallinity.

The predetermined configuration of the illuminating and collected light conditions is characterized by selecting at least one of the following (possibly separately for illumination and collection): excitation wavelength; polarization; retardation; light beam shape; angular distribution of the illuminating light; and wavefront of light.

In some embodiments, the measured data is indicative of a number n (n>1) of Raman spectra obtained from the patterned structure under measurements using the number n of the optical measurement schemes having n different configurations of the illuminating and collected light conditions. The processing of the measured data includes: calculating, for each i-th Raman spectrum of the n Raman spectra, the distribution of Raman-contribution efficiency, $RCE_i(x,y,z)$, across the at least part of the structure under measurements; and selecting one or more distributions of the Raman-contribution efficiency corresponding to the one or more characteristics to be measured; and determining said characteristic(s) of the structure from the selected distribution(s). To clarify, the RCE represents the spatial distribution of the contribution to the Raman signal. It depends on the coupling of electromagnetic radiation into the structure, the excitation of the Raman signal inside the structure and coupling of the excited radiation to the detection system.

The measured data comprising the number n of Raman spectra is obtained in n measurement sessions using the n optical measurement schemes, respectively. Such n measurement schemes may be performed successively; or at least some of such measurement schemes may be performed concurrently.

In another broad aspect of the invention, it provides a method for use in measuring one or more characteristics of patterned structures, the method comprising:

applying a number n of two or more different optical measurement schemes to a patterned structure and determining measured data comprising corresponding n Raman spectra from said patterned structure, said n optical measurement schemes differing from one another in at least one condition of either one or both of illuminating and collected light;

processing the measured data and determining said one or more characteristics of said structure, said processing comprising determining n Raman-contribution efficiency distributions, $RCE_1(x,y,z)$, $RCE_2(x,y,z)$, . . . $RCE_n(x,y,z)$, across at least a part of the structure for said n Raman spectra respectively, each of said Raman-contribution efficiency distributions being dependent on characteristics of the structure and the respective optical measurement scheme, thereby enabling determination of said one or more characteristics of the structure.

In some embodiments, the method of the invention further includes selection of an optimal measurement scheme for determination of one or more characteristics of interest in the patterned structure under measurements. This is implemented by interpreting the Raman-contribution efficiency corresponding to one or more of the preceding measurement schemes and optimizing the configuration of the at least one of the illuminating and collecting light conditions (i.e. optimizing the measurement scheme(s)) for one or more of the successive measurement schemes to be applied to the at least part of the patterned structure.

In yet another broad aspect, the invention provides a control system for use in measuring one or more characteristics of patterned structures. The control system comprises:

a processor unit configured to receive and process measured data comprising data indicative n Raman spectra obtained from a patterned structure under measurements using n optical measurement scheme each with a different configuration of illuminating and collected light conditions corresponding to said one or more characteristics to be measured, said processing of the measured data comprising determining n Raman-contribution efficiency distributions, $RCE_1(x,y,z)$, $RCE_2(x,y,z)$, . . . $RCE_n(x,y,z)$, across at least a part of the structure, for said n Raman spectra respectively, each of said Raman-contribution efficiency distributions being dependent on characteristics of the structure and the respective optical measurement scheme, thereby enabling determination of said one or more characteristics of the structure from a selected one or more of said n Raman-contribution efficiency distributions.

The control system may also include at least one of illumination controller and collection controller configured and operable to controllably vary at least one of the illuminating and collecting light conditions by varying at least one of the following: excitation wavelength; polarization; retardation; light beam shape; angular propagation of the illuminating light; angular propagation of the light being collected; and wavefront of light.

The invention also provides a system for use in measuring one or more characteristics of patterned structures, the system comprising: an optical measurement system configured and operable to perform a number n of different optical measurement schemes on a patterned structure and determining measured data comprising corresponding n Raman spectra from said patterned structure, said n optical measurement schemes differing from one another in at least one condition of either one or both of illuminating and collected light; and the above-described control configured for data communication with the optical measurement system to receive and process the measured data and determine the one or more characteristics of the patterned structure under measurements.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 exemplifies the Raman spectrum from two samples, one being a thin SiGe layer deposited over Si, and the other being a pure bulk Si;

FIG. 2 exemplifies effect of polarization on relative intensity of the single-phonon and two-phonon peaks in Si;

FIG. 3a and FIG. 3b show measured Raman signals from Si grating, corresponding to, respectively, wavelengths of $\lambda=405$ nm and $\lambda=532$ nm;

DETAILED DESCRIPTION OF EMBODIMENTS

Figure 3A:
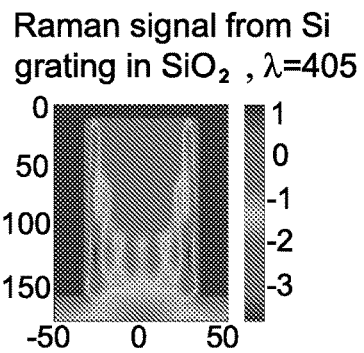
FIGS. 3a to 3c exemplify position-dependence of the contribution to the main-Si-peak in the Raman signal, for a simple grating structure, where FIG. 3c schematically illustrates a modeled structure formed by $SiO_2$ layer on a patterned Si layer.

As indicated above, the present invention is based on the use of Raman Spectroscopy at specific configuration(s) of at least one of illumination and light collection conditions (e.g. polarization(s), excitation wavelength, retardation, light beam shape, angular propagation of the illuminating/collected light, etc.), and preferably in conjunction with suitable modeling capabilities. This technique provides for highlighting and isolating sensitivity to the parameters of interest, and for distinguishing between sensitivity to different material parameters.

The following is the description of optimized Raman metrology scheme, according to some embodiments of the invention.

Raman spectroscopy represents a unique type of light-matter interaction. Different parts of the Raman spectrum have different responses to a change in the optical scheme, specifically: change(s) in illumination and collection polarizations\retardations, change(s) in illumination and collection angle(s) of incidence and pupils shape, wavefronts and focus.

As an example for the possible benefit from correct manipulation of one or more of these parameters, let us consider the issue of two-phonon background. As described previously, the Raman spectrum from pure bulk Si presents a sharp peak at about 520 $cm^{-1}$. An additional, very broad and significantly weaker, spectral peak is observed at 230 $cm^{-1}$-380 $cm^{-1}$. This weak Raman signal arises from a 2-phonon process.

In most cases, the weak Raman signal associated with the 2-photon process is not of interest for the metrology. However, this signal acts as a background signature which can significantly affect (and confound) the interpretation of the Raman spectrum. The relative intensity between the 1-phonon peaks and the 2-phonon peak can be modified by several orders of magnitude through correct control over the illumination and collection polarizations.

This dependence is illustrated in FIG. 2, exemplifying effect of polarization on relative intensity of the single-phonon and two-phonon peaks in Si. Two graphs are shown $P_1$ and $P_2$, where two polarization configurations are presented, i.e. illumination and collection polarizations $P_{ill}||P_{coll}$ (graph $P_1$) and $P_{ill} \perp P_{coll}$ (graph $P_2$). As shown in the figure, when the illumination and collection polarizations $P_{ill}$ and $P_{coll}$ are tuned perpendicular to each other, and both are oriented at 45° to the crystal lattice of a sample, a 3 orders of magnitude suppression of the 2-phonon peak is observed. Thus, by aligning the illumination polarization $P_{ill}$ in direction 45° to the crystal structure, and aligning the collection polarization $P_{coll}$ perpendicular to illumination polarization, the 2-phonon signal is significantly reduced, compared to having the polarizations co-aligned.

This is only one example for how correct polarization manipulation can greatly improve the signal quality and the ability to isolate important measurement components from those which are not of interest (of less interest). As will be described below, the same principle can be used to highlight sensitivity to specific parameters of interest.

Such a simple approach is not practical (and even might be impossible) to be applied to a measured target which is not a planar film but rather is structured. The electromagnetic field distribution inside a structure can be very complicated, and depends on the structure dimensions as well as material characteristics.

The present invention provides for implementing such highlighting of sensitivity and background suppression for not-only blanket targets but rather also on-structure measurements. This can be accomplished by hardware control as well as by utilizing modeling tools to correctly optimize the measurement scheme.

The following are some specific but not limiting examples for such measurement scheme optimization. These examples include: (i) profiling the measured characteristics across the structure: profiling information can be obtained across z (depth profiling), or even full profiling of the measured properties at different locations (x, y and z) across the structure; (ii) metrology measurements of separate stress components inside a structure; (iii) use of modeling/algorithmic tools for during-measurement-feedback; (iv) dimensional metrology.

(i) Profiling of the Measured Characteristics Across the Structure

Raman spectroscopy provides an integral measurement over the probed target: the measured signal averages over the entire measurement spot, and over the penetration depth into the sample. It is often of great interest to be able to identify the distribution of the measured characteristic across the structure, both as a function of depth and of lateral position ("profiling").

It is a common practice to use multiple wavelengths in order to change the penetration depth. The penetration depth dependence on wavelength is very sharp, allowing good resolving capabilities for such profiling method. Penetration depths into Si at normal incidence are exemplified in Table 1.

TABLE 1

| Wavelength [nm] | Penetration depth [nm] |
|---|---|
| 633 | 2600 |
| 532 | 930 |

TABLE 1-continued

| Wavelength [nm] | Penetration depth [nm] |
|---|---|
| 488 | 490 |
| 458 | 280 |
| 405 | 98 |
| 355 | 9.3 |
| 244 | 5.6 |

The values in the table account for the field absorption both in illumination and collection paths.

This method is relatively easy to interpret for planar films, but its application to structured samples can be highly misleading. The electromagnetic (EM) field distribution inside a structure can have a very complicated distribution, dependent in intricate ways on the interaction between the electromagnetic field and the structure characteristics. In these cases, the measured spectrum represents the material properties at those locations in the structure which contribute most to the Raman signal. These indeed depend on the wavelength, but by no means can be easily related to the simple 'penetration depth' concept.

Figure 3B:
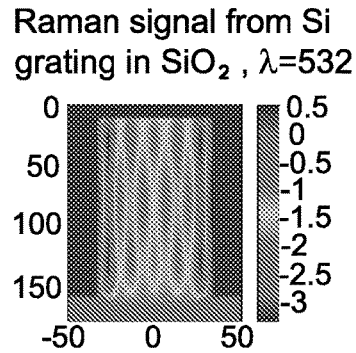
Figure 3C:
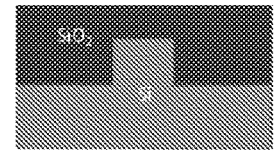

In this connection, reference is made to FIGS. 3a-3c exemplifying position-dependence of the contribution to the main-Si-peak in the Raman signal, for a simple grating structure. FIG. 3c schematically illustrates a modeled structure formed by $SiO_2$ layer on a patterned Si layer. Measured Raman signal from Si grating, corresponding to wavelengths of $\lambda$=405 nm and $\lambda$=532 nm, are shown respectively in FIG. 3a and FIG. 3b. It should be noted that Raman signal only originates from the grating structure (where there is Si), and not from the $SiO_2$ surrounding it.

Figure 4:
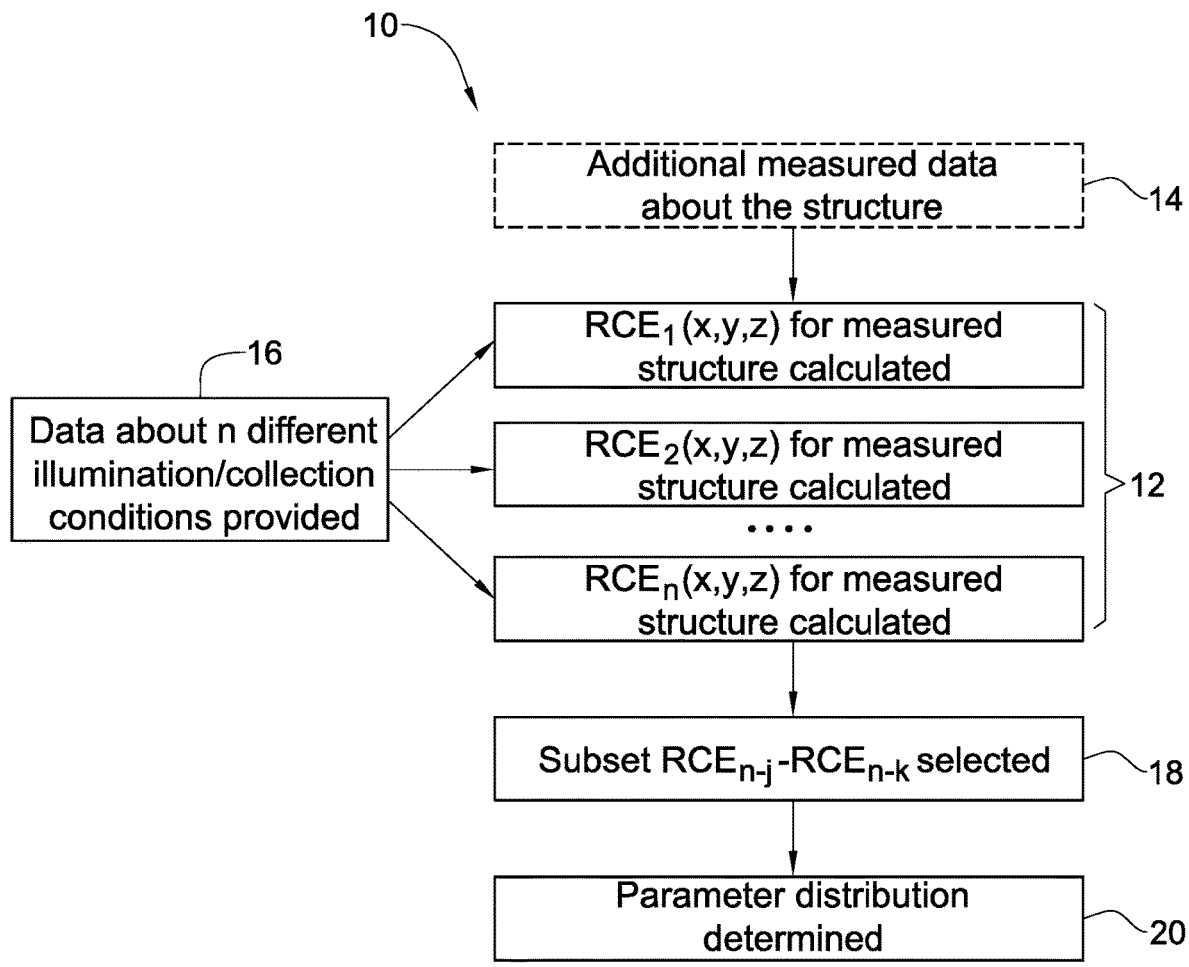
FIG. 4 shows a flow diagram of the Raman spectroscopy model-based method of the invention for use in measurements in patterned structures.

According to the invention, a model-based approach is used, implemented to highly-flexible optical arrangement allowing acquisition of a multiplicity of different information channels, to allow both blanket and on-structure profiling capability (both vs. depth and/or lateral location). In this connection, reference is made to FIG. 4 exemplifying a flow diagram 10 of the model-based method of the invention. For simplicity, this approach can be split into few steps; these are not all necessary for all implementations, some uses not involving all of these steps are described below. However, these step represent the main building blocks of the method of the invention.

First, according to this method a 'Raman-contribution efficiency' (RCE) is defined as specifying the position-dependent contribution to the Raman signal. This property depends on the measured structure characteristics (dimensions, materials), the excitation wavelength and the characteristics of the illumination and collection channels (as will be described below).

Raman-contribution efficiency for a measured structure is calculated (step 12). This calculation may optionally be assisted (step 14) by information about the structure obtained/measured from other metrology tools and/or test sites, e.g. OCD\SEM\TEM to provide dimensional characterization, ellipsometry\XPS\SIMS for material characterization, etc.

Data about a variety of n measurement conditions is provided (step 16), and the Raman-contribution efficiency distributions across the structure $RCE_1(x,y,z)$, $RCE_2(x,y,z)$, ... $RCE_n(x,y,z)$ are calculated for the n measurement conditions, respectively, typically illumination/collection conditions. These may include different angles of incidence (AOIs), wavelengths, polarizations, pupil shaping options, etc. Each different i-th configuration provides a different distribution of the $RCE_i(x,y,z)$ across the structure.

Then, a subset of the calculated configurations, $RCE_{n-j}$–$RCE_{n-k}$, where j and k are integers, j≥k, is chosen (step 18), so as to gain information on the measured parameter distribution. Deriving the parameter distribution inside the structure from the set of measurement (step 20) can be accomplished using standard algorithms (e.g. deconvolution methods).

As an example, a simple approach to implement such derivation can be based on a linear scheme: a set of measured Raman intensities $I_i$ is collected. Each is known to be related to the parameter distribution inside the structure through its RCE, namely:

$$I_i = \int RCE_i(x,y)P(x,y)dxdy.$$

By defining some spatial sampling of the measured structure, this relation can be written in matrix form:

$$I_i = M_{i,j}P_j \text{ or equivalently } \vec{I} = \hat{M}\vec{P}.$$

Here, the index j relates to different spatial locations and the index i relates to a different measurement. As both I and M are known (through the measurement and the modeling engine correspondingly), the spatial distribution of the parameter can be directly obtained using RMS solution:

$$\vec{P} = \hat{M}^{-1}\vec{I}.$$

Many other algorithmic methods are available, allowing more stable and well-controlled solutions.

This methodology can be applied to any measurable property, such as stress, composition, crystallinity, which are just a few non-limiting examples.

It should be noted that the above-exemplified technique does not necessarily has to be applied to a set of measurements. In practice, this approach can be used to find a single, optimized measurement scheme providing highlighted sensitivity to a parameter of interest. The principles of the invention do not relate to obtaining full across-structure profile information using a single measured Raman spectrum, but this way the most important information can be gained with short acquisition times. Alternatively, simultaneous acquisition of Raman spectra for multiple AOIs can be measured using k-space imaging techniques.

Figure 5:
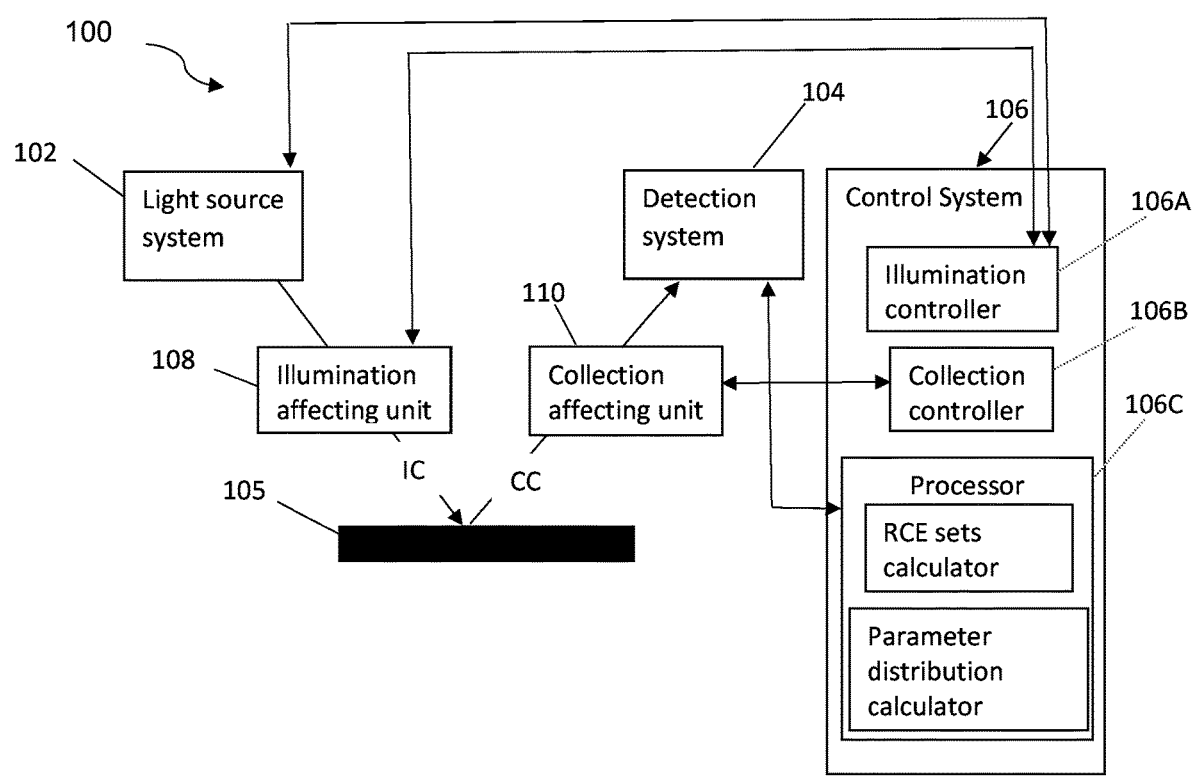
FIG. 5 showing a block diagram of a system of the invention for carrying out the method of FIG. 4 for interpreting Raman metrology measured data (and possibly also managing Raman metrology measurements)

This is exemplified in FIG. 5 showing a block diagram of a measurement system 100 utilizing flexible Raman metrology measurement schemes. As described, such flexibility used in conjunction with advanced modeling tools, allows the improved performance, as well as altogether new capabilities (e.g. profiling). System 100 includes a control system 106 which is configured to receive input measured data indicative of Raman spectrum or spectra measured on at least a part of a sample 105 using one or more measurement schemes implemented in an optical system; and process this measured data by performing the above-described technique of the invention.

Generally, the measured data may be processed and analyzed in real time, in which case the control system 106 may receive the measured data directly from the output of the optical measurement system; or may be analyzed off line in which case the measured data source may be constituted by an externa storage device. For example, the measured data from a specific type of structure may be analyzed off line, this pre-calculated data may form a parameter-dependent 'library' of theoretical spectra, in order to select the predetermined (optimal) measurements scheme for measuring structure parameter(s) of interest to be used for controlling the process of manufacture of the structures of said type.

The optical measurement system includes a light source system 102 defining an illumination channel IC, and a detection system 104 defining a collection channel CC, and also includes a light affecting unit located in/associated with at least one of illumination and collection channels. In this non limiting example, the system includes both a light illumination affecting unit 108 and a light collection affecting unit 110. The Illumination and collection affecting units are configured for affecting illumination and collection conditions. Such unit may include light propagation affecting optics for affecting the condition of light propagating along the respective channel. The illumination affecting unit 108 may include (e.g. in addition to the light propagation affecting optics) a controller for controlling operation of a light source system; alternatively or additionally such controller may be part of the control system 106.

The control system 106 is generally a computer system configured for communication with measured data provider (this may be wires and/or wireless communication, using any known suitable technique); and may also be configured for managing/controlling the measurements with different measurement schemes in which case the control unit is also configured to communicate with at least some elements of the optical measurement system (this may be wires and/or wireless communication, using any known suitable technique). As shown in the present example, the control system 106 may include illumination controller 106A associated with the illumination affecting unit 108 and/or light source system 102; a collection controller 106B associated with the collection affecting unit 110; and a data processor utility 106C. The latter is configured (preprogrammed with a specifically designed software product) to carry out the above-described method for processing data indicative of measured Raman spectrum or spectra and determining the parameter(s) distribution inside the sample 105.

Figure 6:
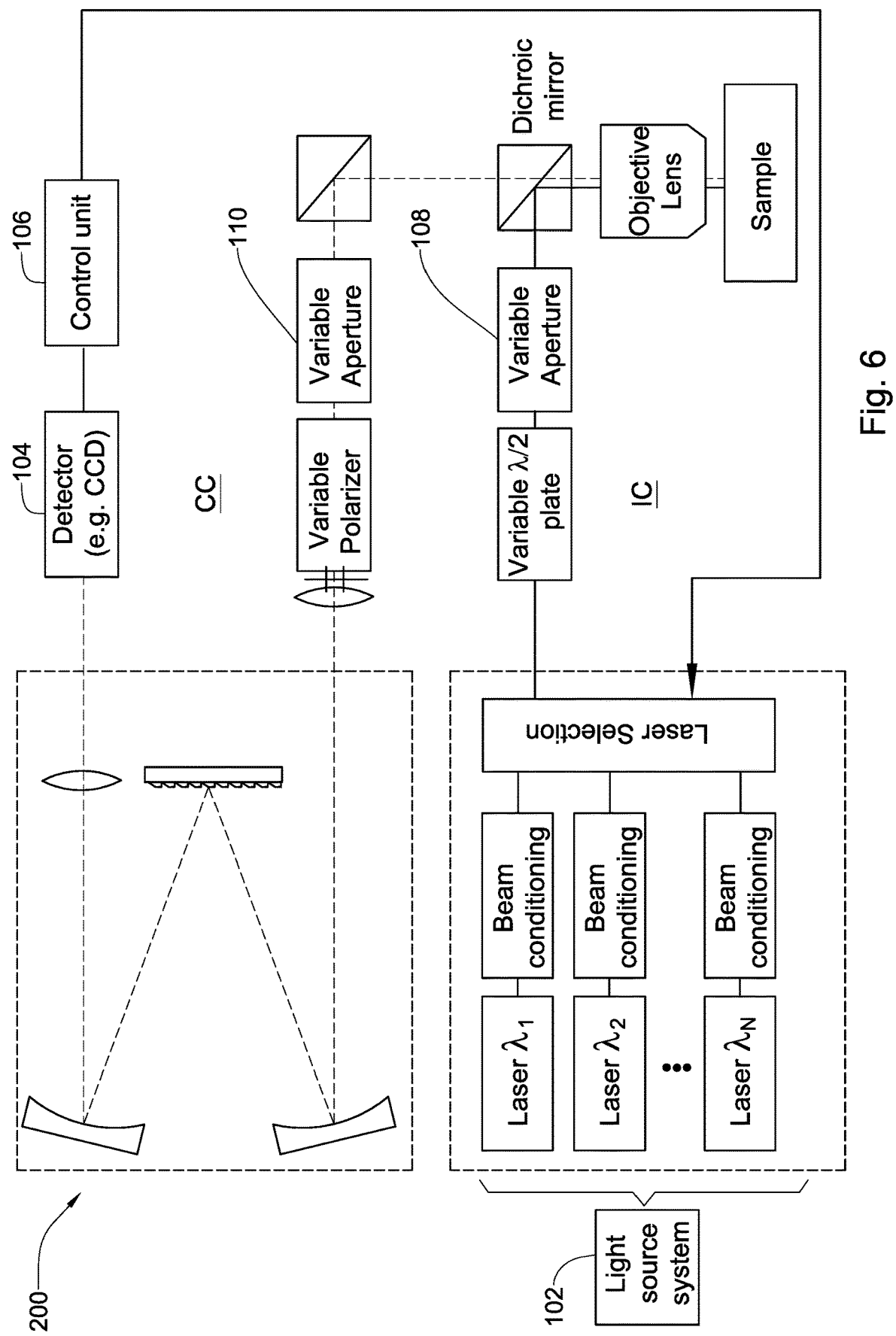
FIG. 6 illustrates a specific but not limiting example of the configuration of the optical measurement system allowing considerable flexibility of measurement schemes, to be used with the control system of FIG. 5.

The efficiency of the above described approach depends on the measurement flexibility allowed by the measurement system. Degrees of freedom added to the optical path can allow improved fine tuning of the measurement to the requested metrological aim. FIG. 6 illustrates, in a self-explanatory manner, specific but not limiting example of the configuration of the optical system 200 allowing such considerable flexibility, including polarization control (including measurement of full Raman-Mueller matrix), pupil shaping at illumination and collection, multiple wavelengths, k-space imaging etc. To facilitate understanding the main functional assemblies that are common in the FIGS. 5 and 6 are identified by the same reference numbers.

In system 200 of FIG. 6, the light source system 102 includes n light sources (e.g. lasers) each for generating a light beam of a different wavelengths; and includes/is associated with n beam conditioning units in light paths of the n light beams, respectively; and a laser beam selection unit (being optical and/or electronic unit) for selecting the excitation (illuminating) wavelength. The beam conditioning can include spectral filtering and/or polarization and/or spatial filtering and/or beam expansion and/or collimation. Such beam conditioning units are part of the illumination affecting unit 108. In this example, the illumination affecting unit 108 further includes polarization rotation assembly (e.g. variable λ/2 plate) and aperture variation assembly. In other words, the illumination affecting unit 108 is configured to enable variety of illumination wavelengths, polarization conditions, and angular propagation of the illumination. The collection affecting unit 110 is configured to provide variety of polarization conditions, spectral filtering and angular propagation of the light being collected from the sample.

(ii) Metrology of Stress Distribution Inside a Structure, Allowing Separation of Different Stress Components Stress metrology is a standard aim for Raman spectroscopy. The crystal strain, accompanying internal stress, affects the inter-atomic forces, leading to a corresponding change in the vibration frequencies. These changes are directly probed by Raman spectroscopy, through the shift in the Raman peaks locations. Different methods exist to separate stress/strain from other characteristics which affect the peaks locations (e.g. composition, doping).

It can be shown that normal-incidence Raman metrology is predominantly sensitive to the z component of the crystal strain (G. H. Loechelt et al., *Polarized off-axis Raman spectroscopy: A technique for measuring stress tensors in semiconductors*, J. App. Phys. 86, 6164 (1999)). For simple non-patterned films, some sensitivity to the in-plain strain components can be obtained using oblique illumination and/or collection channels, or very high numerical aperture measurement setups. However, these methods are completely irrelevant when measuring in patterned structures.

Similarly to the methodology described above for spatial profiling, the present invention provides for using modeling tools, in conjunction with selected modes of measurement (illumination/collection AOI and pupil shaping, wavelengths, polarizations, etc.), to identify a preferred metrology scheme (or combination of such schemes) to provide optimal sensitivity to the strain orientation(s) of interest. Alternatively, it is possible to identify the optimal metrology scheme experimentally, by first utilizing a large set of varied measured information channels, and then identification of the most beneficial set (that one which provides best precision, accuracy and/or any other attribute).

The full vectorial strain distribution inside the structure can be derived from a set of such measurements using standard algorithms. For clarity, a possible approach is exemplified below, while it should be understood that many other algorithmic methods can be implemented. The same approach can be used in an identical manner for across-structure profiling of any other property to which the Raman signal is sensitive (e.g. composition, doping).

Each measured dataset for RCE depends on the strain distribution through some known weighting over different parts of the structure (this weight is known based on the modeling tool). Explicitly, we can write:

$$I(C_i) = \int RCE^{C_i}(x,y,z) S[P(x,y,z)] dx dy dz$$

Here, $C_i$ represents the measured channel/measurement scheme defined by a configuration of illuminating and collected light conditions (AOI, polarizations, azimuths, etc.); (x,y,z) are the spatial coordinates; $RCE^{C_i}$ is the Raman Contribution Efficiency for this channel, defined above; P is the position-dependent parameter (strain in the present case); and $S[P(x, y, z)]$ is the associated Raman signal for this distribution of the parameter, obtained by modeling.

The rationale behind this expression is that the Raman signal sums over the individual contributions from different parts of the structure, with each contribution being dependent on the local strain, and weighed according to the local RCE. It should be noted that this expression is an approximation for the more rigorous derivation, and is used here for simplicity, to clarify the proposed method for strain distribution characterization.

In matrix form, this expression can be written as $$I_i = \overrightarrow{RCE_i} \cdot \vec{S}[P],$$

where the index i stands for the measured channel, and the vectorization is across the entire spatial domain (i.e. different entries in the vectors correspond to different positions).

Considering now a set of measured channels, leading to a set of measured signals $\vec{I}$, we can write $$\vec{I} = \widehat{RCE} \cdot \vec{S}[P],$$

where $\widehat{RCE}$ is a matrix holding the weighting across structure for each measured channel, known from the model.

Using the measured signal $\vec{I}$ and the calculated $\widehat{RCE}$, the spatial strain distribution can be estimated using $$\vec{S}[P] = (\widehat{RCE})^{-1} \cdot \vec{I}.$$

(iii) Use of Modeling/Algorithmic Tools for During-Measurement-Feedback

The approach described above concerns the use of modeling capabilities to pre-define a measurement sequence for the application of interest, namely what channel combination to use, how to optimize the measurement sequence, etc. This approach can be extended to allow modifications to the measurement flow according to the measured results. Several variations are possible for this implementation, as follows:

The interpreted results from a previous Raman measurement can be used. More specifically, a first set of Raman measurements (one or several) provides information on the measured characteristics. Using modeling capabilities, it is then possible to change the measurement characteristics (wavelength, AOI, polarizations, etc.) so as to provide improved performance of the measurement. This method can be implemented for consecutive measurements performed on other sites, or for repeated measurements on the same site.

An example of specific interest for such usage of metrological feedback is the identification of stress relaxation. When growing a crystalline layer (e.g. epitaxially-grown SiGe or GaAs) on a substrate made out of a different material (e.g. Si), crystal strain is developed due to the different crystal lattice constants. Depending on the growth conditions and the layer thickness, strain relaxation can potentially occur, in the form of alternating relaxed and strained regions. Such strain relaxation can be disastrous to the performance of the fabricated device, and requires adequate monitoring. Such metrology can be provided using Raman spectroscopy based on the concept of during-measurement-feedback, as follows: Local strain and composition can be deduced from the Raman measurement. In extreme cases, this measurement alone may be enough to identify significant strain relaxation. However, if relaxation is not overly severe, the measurement will only identify that relaxation is suspected. Using a model-based tool, the strain reading can be analyzed to identify such relaxation-suspected cases. Modeling is especially critical for on-structure measurements, when different strain components can confound the measurement. When a sample suspected of strain relaxation is identified, another set Raman measurements can be taken at adjacent locations. As noted, it is a typical characteristic of strain-relaxed samples that the strain becomes inhomogeneous, expressing regions of high and low strain. If indeed such variability is identified, the sample will be classified as strain-relaxed.

(iv) Dimensional Metrology

One capability of unique interest allowed by adding modeling capabilities to Raman spectroscopy is dimensional metrology. Indeed, such capabilities require a multifaceted modeling tool/methods, involving both comprehensive characterization of the electromagnetic field penetration into and out of the structure, as well as modeling of the Raman signal creation inside the structure. Such a path can provide highly sensitive information on the measured structure.

Evidence that dimensional factors affect the measured Raman signal are known in the literature, for example from the following publications: A. K. Arora et al., *Raman spectroscopy of optical phonon confinement in nanostructured materials*, J. of Raman Spectroscopy 38, 604 (2007); B. Kaleli et al., *Strain characterization of FinFETs using Raman spectroscopy*, Thin Solid Films 31497 (2013); T. Nuytten et al., *Edge-enhanced Raman scattering in narrow sGe fin field-effect transistor channels*, App. Phys. Lett. 106, 033107 (2015). On specific cases (e.g. nanowires), the Raman signal has been found to provide dimensional information on a dimensional characteristic of the structure (e.g. nanowire diameter [J. Liu et al., *Raman spectrum of array-ordered crystalline silicon nanowires*, Physica E 23, 221 (2004); R. P. Wang et al., *Raman spectral study of silicon nanowires: High-order scattering and phonon confinement effects*, Phys. Rev. B 61, 16827 (2000)]).

However, through general modeling capabilities, akin to that utilized in OCD metrology, a similar methodology to OCD can be used to solve the inverse-problem of deducing the dimensional properties from the measurements. In this method, the measured signal is compared to that calculated from the modeling tool, for some assumed properties (dimensions, materials) of the test structure. When good fit is obtained between the measured and calculated signal, it is deduced that the measured structure has similar characteristics to the corresponding calculated one. Similarly to common practice in OCD metrology, the theoretical Raman signals can be calculated in real-time ('real-time regression') or pre-calculated to form a parameter-dependent 'library' of theoretical spectra.

The invention claimed is:

1. A method for use in measuring one or more characteristics of patterned structures, the method comprising:
    providing measured data comprising data indicative of at least one Raman spectrum obtained from a patterned structure under measurements using at least one selected optical measurement scheme each with a pre-determined configuration of at least one of illuminating and collected light conditions corresponding to said one or more characteristics to be measured;
    processing the measured data, and determining, for each of said at least one Raman spectrum, a distribution of Raman-contribution efficiency (RCE) within at least a part of the structure under measurements, being dependent on characteristics of the structure and said predetermined configuration of the at least one of illuminating and collected light conditions in the respective optical measurement scheme; and
    analyzing said distribution of Raman-contribution efficiency and determining said one or more characteristics of the structure,
    wherein said measured data is indicative of a number n (n>1) of Raman spectra obtained from said patterned structure under measurements using the number n of the optical measurement schemes having n different configurations of the at least one of the illuminating and collected light conditions; said processing of the measured data comprising: for each i-th Raman spectrum of said n Raman spectra, calculating the distribution of Raman-contribution efficiency, $RCE_i(x,y,z)$, across said at least part of the structure under measurements; and selecting one or more distributions of the Raman-contribution efficiency corresponding to said one or more characteristics to be measured; and determining said one or more characteristics of the structure, wherein said measured data comprising the number n of Raman spectra is obtained in n measurement sessions using said n optical measurement schemes, respectively, and wherein said n measurement sessions are performed successively; and selecting an optimal measurement scheme for determination of one or more characteristics of interest in the patterned structure under measurements, wherein said selecting of the optimal measurement scheme comprises: interpreting the Raman-contribution efficiency corresponding to one or more of preceding measurement schemes and optimizing the configuration of said at least one of the illuminating and collecting light conditions for one or more of the successive measurement schemes to be applied to the at least part of the patterned structure.

2. The method according to claim 1, wherein said one or more characteristics of the structure to be measured comprises at least one of the following: dimension, material composition, stress, crystallinity.

3. The method according to claim 1, wherein the predetermined configuration of the at least one of illuminating and collected light conditions is characterized by selecting at least one of the following: excitation wavelength; polarization; retardation; light beam shape; angular propagation of the illuminating light; angular propagation of the light being collected; and wavefront of light.

4. The method according to claim 1, wherein said calculating of the distribution of the Raman-contribution efficiency for each of the n Raman spectra comprises processing additional measured data obtained by one or more measurements of a type different from Raman spectroscopy, applied to said structure or a corresponding test structure.

5. A method for use in measuring one or more characteristics of patterned structures, the method comprising:

providing measured data comprising data indicative of at least one Raman spectrum obtained from a patterned structure under measurements using at least one selected optical measurement scheme each with a predetermined configuration of at least one of illuminating and collected light conditions corresponding to said one or more characteristics to be measured;

processing the measured data, and determining, for each of said at least one Raman spectrum, a distribution of Raman-contribution efficiency (RCE) within at least a part of the structure under measurements, being dependent on characteristics of the structure and said predetermined configuration of the at least one of illuminating and collected light conditions in the respective optical measurement scheme; and analyzing said distribution of Raman-contribution efficiency and determining said one or more characteristics of the structure, wherein said measured data is indicative of a number n (n>1) of Raman spectra obtained from said patterned structure under measurements using the number n of the optical measurement schemes having n different configurations of the at least one of the illuminating and collected light conditions; said processing of the measured data comprising: for each i-th Raman spectrum of said n Raman spectra, calculating the distribution of Raman-contribution efficiency, $RCE_i(x,y,z)$, across said at least part of the structure under measurements; and selecting one or more distributions of the Raman-contribution efficiency corresponding to said one or more characteristics to be measured; and determining said one or more characteristics of the structure, wherein said measured data comprising the number n of Raman spectra is obtained in n measurement sessions using said n optical measurement schemes, respectively, and wherein said n measurement sessions are performed successively; and selecting an optimal measurement scheme for determination of one or more characteristics of interest in the patterned structure under measurements, wherein said selecting of the optimal measurement scheme comprises: interpreting the Raman-contribution efficiency corresponding to one or more of preceding measurement schemes and optimizing the configuration of said at least one of the illuminating and collecting light conditions for one or more of the successive measurement schemes to be applied to the at least part of the patterned structure, and wherein said one or more preceding measurement schemes and said one or more successive measurement schemes with the optimized configuration of said at least one of the illuminating and collecting light conditions are applied to the same measurement site or different measurement sites in said structure.

6. The method according to claim 5, wherein said one or more characteristics of the structure to be measured comprises at least one of the following: dimension, material composition, stress, crystallinity.

7. The method according to claim 5, wherein the predetermined configuration of the at least one of illuminating and collected light conditions is characterized by selecting at least one of the following: excitation wavelength; polarization; retardation; light beam shape; angular propagation of the illuminating light; angular propagation of the light being collected; and wavefront of light.

8. The method according to claim 5, wherein said calculating of the distribution of the Raman-contribution efficiency for each of the n Raman spectra comprises processing additional measured data obtained by one or more measurements of a type different from Raman spectroscopy, applied to said structure or a corresponding test structure.

9. A system for use in measuring one or more characteristics of patterned structures, the measurement system comprising:

an optical measurement system configured and operable to perform a number n of different optical measurement schemes on a patterned structure and determining measured data comprising corresponding n Raman spectra from said patterned structure, said n optical measurement schemes differing from one another in at least one condition of either one or both of illuminating and collected light; and a control system for use in measuring one or more characteristics of patterned structures, the control system comprising a processor unit configured to receive and process measured data comprising data indicative n Raman spectra obtained from a patterned structure under measurements using n optical measurement scheme each with a different configuration of at least one of illuminating and collected light conditions corresponding to said one or more characteristics to be measured, said processing of the measured data comprising determining n Raman-contribution efficiency distributions, $RCE_1(x,y,z)$, $RCE_2(x,y,z)$, ... $RCE_n(x,y,z)$, across at least a part of the structure, for said n Raman spectra respectively, each of said Raman-contribution efficiency distributions being dependent on characteristics of the structure and the respective optical measurement scheme, thereby enabling determination of said one or more characteristics of the structure from a selected one or more of said n Raman-contribution efficiency distributions, wherein the control system is configured for data communication with the optical measurement system to receive and process the measured data and determine said one or more characteristics of the patterned structure under measurements, and wherein said optical measurement system is configured to perform said n different measurement schemes successively by controllably varying at least one of the illuminating and collecting light conditions by varying at least one of the following: excitation wavelength; polarization; retardation; light beam shape; angular propagation of the illuminating light; angular propagation of the light being collected; and wavefront of light.

10. The system according to claim 9, wherein said optical measurement system is configured to concurrently perform at least some of said n measurement sessions.

11. The system according to claim 9, wherein said one or more characteristics of the structure to be measured comprises at least one of the following: dimension, material composition, stress, crystallinity.

12. The system according to claim 9, configured for operating an optical measurement system for performing said n different optical measurement schemes.

13. The system according to claim 12, comprising at least one illumination controller and collection controller configured and operable to controllably vary the at least one of the illuminating and collecting light conditions by varying at least one of the following: excitation wavelength; polarization; retardation; light beam shape; angular propagation of the illuminating light; angular propagation of the light being collected; and wavefront of light.

* * * * *